United States Patent
Blazejewski

(10) Patent No.: US 11,471,032 B2
(45) Date of Patent: Oct. 18, 2022

(54) ENDOSCOPE

(71) Applicant: Blazejewski MEDI-TECH GmbH, Sexau (DE)

(72) Inventor: Reinhold Blazejewski, Gutach (DE)

(73) Assignee: Blazejewski MEDI-TECH GmbH, Sexau (DE)

( * ) Notice: Subject to any disclaimer, the term of this patent is extended or adjusted under 35 U.S.C. 154(b) by 238 days.

(21) Appl. No.: 16/761,857

(22) PCT Filed: Dec. 19, 2018

(86) PCT No.: PCT/DE2018/101032
§ 371 (c)(1),
(2) Date: May 6, 2020

(87) PCT Pub. No.: WO2019/120384
PCT Pub. Date: Jun. 27, 2019

(65) Prior Publication Data
US 2021/0196107 A1      Jul. 1, 2021

(30) Foreign Application Priority Data
Dec. 21, 2017   (DE) ..................... 10 2017 130 905.5

(51) Int. Cl.
*A61B 1/00* (2006.01)
*A61B 1/018* (2006.01)

(52) U.S. Cl.
CPC .......... *A61B 1/018* (2013.01); *A61B 1/00071* (2013.01); *A61B 1/00165* (2013.01)

(58) Field of Classification Search
None
See application file for complete search history.

(56) References Cited

U.S. PATENT DOCUMENTS 5,213,093 A      5/1993   Swindle
9,119,531 B2 *   9/2015   Surti .................... A61B 1/0008
(Continued)

FOREIGN PATENT DOCUMENTS

DE      10 2016 109 066 A1      11/2017

OTHER PUBLICATIONS

International Search Report in PCT/DE2018/101032, dated Jun. 13, 2019.

(Continued)

*Primary Examiner* — Timothy J Neal
(74) *Attorney, Agent, or Firm* — Collard & Roe, P.C.

(57) ABSTRACT

An endoscope is proposed with a shaft (2) that is designed as a flexible or rigid elongated hollow body with a main body (3) which houses the shaft (2) on its proximal end (5) with an image guide (7) and a working channel (10) which extend through the shaft (2) from the distal to the proximal end, continuing into the main body (3) wherein the working channel (10) receives an instrument with a distal end (11) of the working channel (10) which is located in the area of the distal end (6) of the shaft (2) with a proximal end (12) of the working channel (10) which is located in or on the main body (3) wherein the cross-section of the working channel (10) is circular at its proximal end (12) and non-circular at its distal end (11) and wherein the working channel (10) has a transitional area (18) in which the circular cross-section transitions into the non-circular cross-section.

12 Claims, 6 Drawing Sheets

(56) References Cited

U.S. PATENT DOCUMENTS

Figure 1:
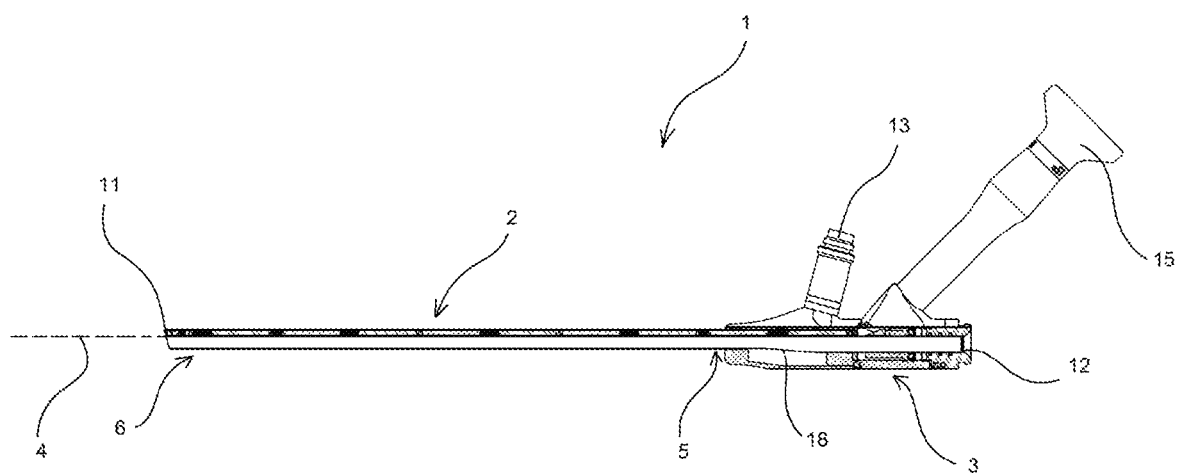

2008/0045787 A1     2/2008   Snay et al.
2009/0118577 A9*   5/2009   Snay ................. A61B 1/00071
                                                                                              600/109
2017/0332893 A1    11/2017   Irion et al.

OTHER PUBLICATIONS

International Preliminary Report on Patentability in PCT/DE2018/101032, dated Jun. 25, 2020.

* cited by examiner

ENDOSCOPE

CROSS REFERENCE TO RELATED APPLICATIONS

This application is the National Stage of PCT/DE2018/101032 filed on Dec. 19, 2018, which claims priority under 35 U.S.C. § 119 of German Application No. 10 2017 130 905.5 filed on Dec. 21, 2017, the disclosure of which is incorporated by reference. The international application under PCT article 21(2) was not published in English.

The invention relates to a method with a shaft, a main body which houses the shaft on its proximal end, an image guide and a working channel which extend through the shaft from the distal to the proximal end, continuing into the main body.

Endoscopes are used both in the technical and the medical sector. They are used to examine structures on the surface or in difficult to access cavities, channels or recesses. The naked eye is often insufficient to resolve these structures. In the medical sector, endoscopes are used in minimally invasive surgery for examination purposes or in combination with surgical instruments for operations under visual inspection. A lighting system can be used to illuminate the structures to be examined. The light generated by an external light source is usually transmitted to the structure to be examined via fibre-optic light guides, particularly via optical fibres. The fibre-optic light guide can be integrated into the endoscope. An imaging system is used to capture the information that is contained in the light reflected by the structure as an image. An image converter chip, such as CMOS or CCD, is frequently used as the camera or image sensor. The image sensor, also called an image generator, converts the optical signals into electrical signals which are then made optically visible on a screen or a monitor. Alternatively, or additionally the endoscope may be equipped with an eyepiece.

On known endoscopes, the image generator or image generators are arranged at the proximal or distal end. The endoscope comprises a flexible or rigid shaft that has the form of an elongated hollow body and a main body which houses the shaft on its proximal end. The shaft is guided into a cavity to be examined. The shaft extends along a longitudinal axis that runs lengthways. The external cross-section of the shaft is preferably rounded, and in particular circular. The main body is used to handle the endoscope. The light reflected by a structure to be examined is input at the distal end of the shaft via a lens and fed via an optical image guidance system with optical components such as lenses and prisms or through an optical fibre to the image generator. The image generator is also called the image sensor. The image guide comprises the lens on the distal end of the shaft, the optical image guidance system and the image generator. If the image sensor is arranged at the distal end of the shaft, the electrical signals generated by the image sensor from the reflected light are guided via a signal line to the proximal end of the shaft and into the main body. This signal line is also part of the image guide. The images captured by the image sensor are processed by image processing equipment and visually displayed for the user on a display unit.

In addition to an image guide and a fibre-optic light guide, known endoscopes have a working channel. The image guide and working channel extend from the main body through the shaft to its distal end. An instrument is inserted into the working channel. The working channel has an opening through which the instrument is inserted on its proximal end at the main body. The instrument is moved through the working channel to the distal end of the shaft in order to process a structure observed using the image guide. These types of instruments include, for example, pliers, grippers or shears. They are used to grip, hold, cut, punch, pinch or otherwise manipulate the structure.

If the endoscope is to be used for the examination of structures in small cavities, the diameter of the shaft, particularly at the distal end, must be as small as possible. The diameter of the shaft must be smaller than that of the cavity in which the endoscope is to be inserted. This in turn means that the cross-section of the working channel running through the shaft must be even smaller, as a result of which the instruments used in the working channel must also have a small diameter. Additionally, instruments such as pliers, grippers or shears can remove pieces from the processed structure and pick these up. These pieces are pinched or clamped in the instrument and guided out of the working channel together with the instrument. If a piece of this kind is pinched at the instrument, this may increase the diameter of the instrument accordingly.

The invention is based on the task of providing an endoscope with working channel for an instrument on which the shaft for introduction into cavities has the smallest diameter possible and the working channel running through the shaft still has a sufficient cross-section for the handling of instruments and which also in particular enables the withdrawal of the instrument through the working channel if the instrument removes a piece of a structure to be examined and clamps it in such a way that the piece is guided out of the working channel together with the instrument while the shaft of the endoscope remains in the cavity.

This object is achieved by an endoscope having the features of claim 1. It is characterised in that the working channel has a circular cross-section at its proximal end and a non-circular cross-section at its distal end. The proximal end of the working channel is located at or in the main body. The endoscope is inserted into the cavity to be examined with the distal end first. The main body remains outside of the cavity. There is thus sufficient space available for the section of the working channel that runs into the main body. The working channel has a circular cross-section at the proximal end which facilitates the insertion of an instrument into the working channel at its proximal end. Corresponding cavities can also be created easily and comparatively low cost. At its distal end, the cross-section of the working channel is non-circular. Due to this shape of the working channel at the distal end, there is sufficient space within the shaft itself even at small shaft diameters within the shaft next to the working channel for an image guide and if necessary additional space for one or more fibre-optic light guides and for one or more flushing channels, if necessary. The shaft itself can have a circular external cross-section for the insertion in the cavity and the alignment in a cavity.

The working channel preferably has a cross-section with a constant cross-section area in the section of the shaft that can be inserted into a cavity. This means that the shape and size of the cross-section area of the working channel does not change in the relevant section of the shaft. As a result, the shaft also has a constant cross-section area in this section.

The non-circular cross-section of the working channel has a greatest diameter and a smallest diameter. An instrument that has a smaller diameter than the smallest diameter of the non-circular cross-section of the working channel when inserted into the working channel before processing a structure can be turned after picking up a piece in such a way that it can travel through the greatest diameter of the relevant section of the working channel when moving back out of the working channel. This guarantees that the instrument can also be pulled out if the instrument has picked up a piece of the structure to be processed. Removal of the entire endoscope from the cavity is not necessary in this case. This is of significant benefit during medical applications in particular as repeated insertion and withdrawal of the entire shaft into and out of a cavity increases the risk of injury and infection.

Between the proximal end with circular cross-section and the distal end with non-circular cross-section the working channel has a transitional area in which the circular cross-section transitions into the non-circular cross-section. Advantageously, the cross-section changes continuously in the transitional area so that a wall bordering the working channel forms a ramp or a type of funnel along which an instrument can slide during insertion into the working channel. Wedging is thereby avoided. As an alternative, the transitional area can form one or several steps.

Despite a shaft with a small diameter, particularly on the distal end, the endoscope according to the invention thereby has a working channel that can accommodate an instrument even if this has a slightly larger diameter than the smallest diameter of the oval section of the working channel. This is particularly the case if the instrument has picked up a piece of the structure to be processed that is to be moved out of the working channel together with the instrument. At the same time, the working channel has a circular cross-section at its proximal end, thereby facilitating insertion of an instrument. The instrument can be turned as needed during insertion in the working channel.

According to an advantageous embodiment of the invention, the cross-section area of the working channel is larger at the proximal end than at the distal end.

According to a further advantageous embodiment of the invention, the section of the working channel that extends beyond the main body into the shaft has a continuous non-circular cross-section with a constant cross-section area. As a result, the shaft outside the main body also has a continuously consistent cross-section with a constant cross-section area. This facilitates the insertion of the shaft into a cavity.

According to a further advantageous embodiment of the invention, the working channel has a continuous circular cross-section with a constant cross-section area between the transitional area and the proximal end.

According to a further advantageous embodiment of the invention, the transitional area is generally conical or tapered.

According to a further advantageous embodiment of the invention, the transitional area is located in the main body.

According to a further advantageous embodiment of the invention, the non-circular cross-section area of the working channel at its distal end has a greatest diameter and a smallest diameter. The greatest diameter is smaller than or equal to the diameter of the circular cross-section area of the working channel at its proximal end.

According to a further advantageous embodiment of the invention, the centre point of the non-circular cross-section area of the working channel at its distal end corresponds to the point of intersection from the greatest diameter and the smallest diameter.

According to a further advantageous embodiment of the invention, the working channel has a first working channel longitudinal axis in its section with non-circular cross-section that extends through the centre points of the non-circular cross-section areas. The working channel further has a second working channel longitudinal axis in its section with circular cross-section that extends through the centre points of the circular cross-section areas.

According to a further advantageous embodiment of the invention, the extension of the first working channel longitudinal axis coincides with the second working channel longitudinal axis.

According to a further advantageous embodiment of the invention, the extension of the first working channel longitudinal axis is parallel to the second working channel longitudinal axis and has a distance a from the second working channel longitudinal axis that is not zero. The two working channel longitudinal axes are thereby laterally offset from one another.

According to a further advantageous embodiment of the invention, the distance 'a' is less than or equal to the difference from half of the diameter of the circular cross-section area of the working channel at its proximal end and half of the smallest diameter of the non-circular cross-section area of the working channel at its distal end.

According to a further advantageous embodiment of the invention, the non-circular cross-section is rounded. The cross-section thereby has no corners. This has the advantage that a tool introduced into the working channel cannot become wedged during insertion and removal or other movement in the working channel. The shape of the cross-section can be oval or kidney-shaped, for example.

According to a further advantageous embodiment of the invention, the non-circular cross-section at the distal end of the working channel is oval. The cross-section is thus rounded but not circular. The oval shape is characterised in that both the smallest diameter and the greatest diameter are located entirely within the cross-section area.

Further advantages and advantageous embodiments of the invention can be obtained from the following description, the drawing and the claims.

DRAWING

The drawing shows a model embodiment of the invention. Illustrations:

FIG. 1 Endoscope in a longitudinal section

Figure 2:
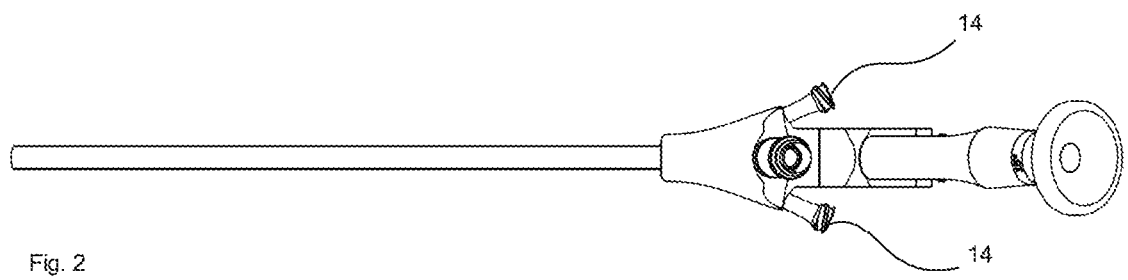

FIG. 2 Endoscope according to FIG. 1 in a view from above

Figure 3:
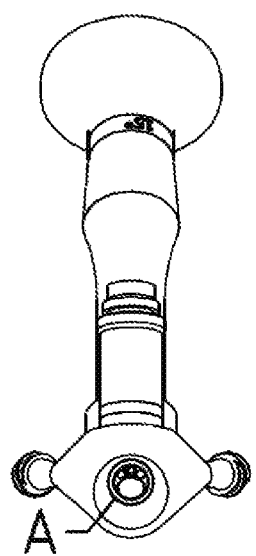

FIG. 3 Endoscope according to FIG. 1 in a view from the front

Figure 4:
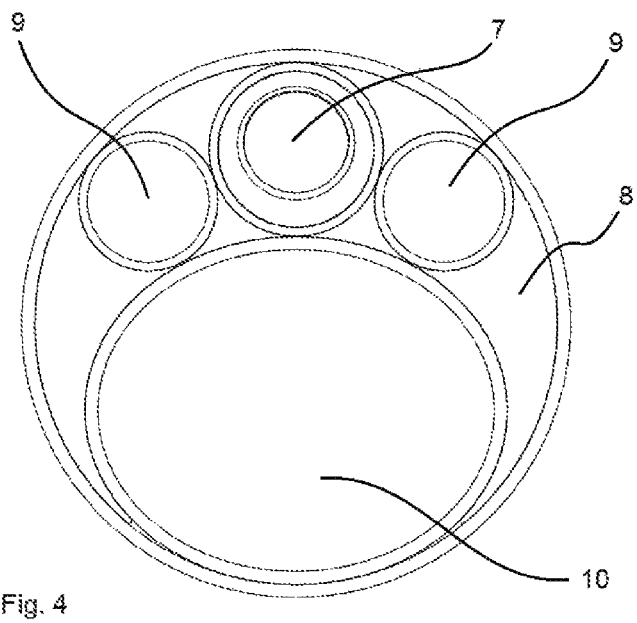
Figure 6:
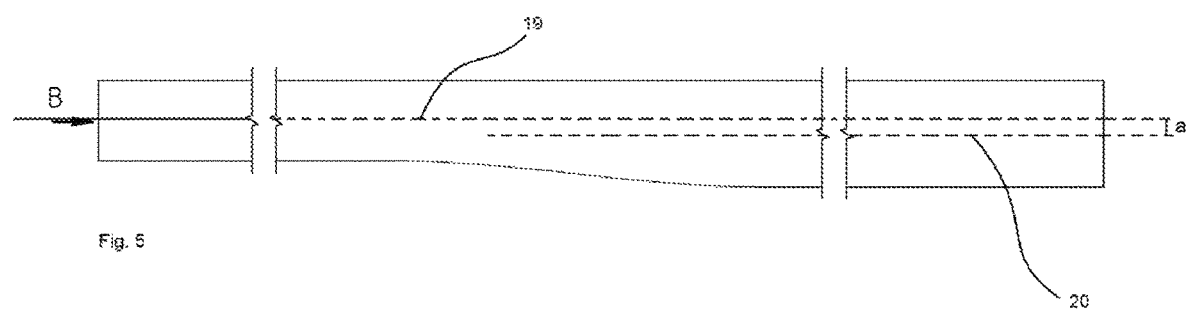
Figure 6:
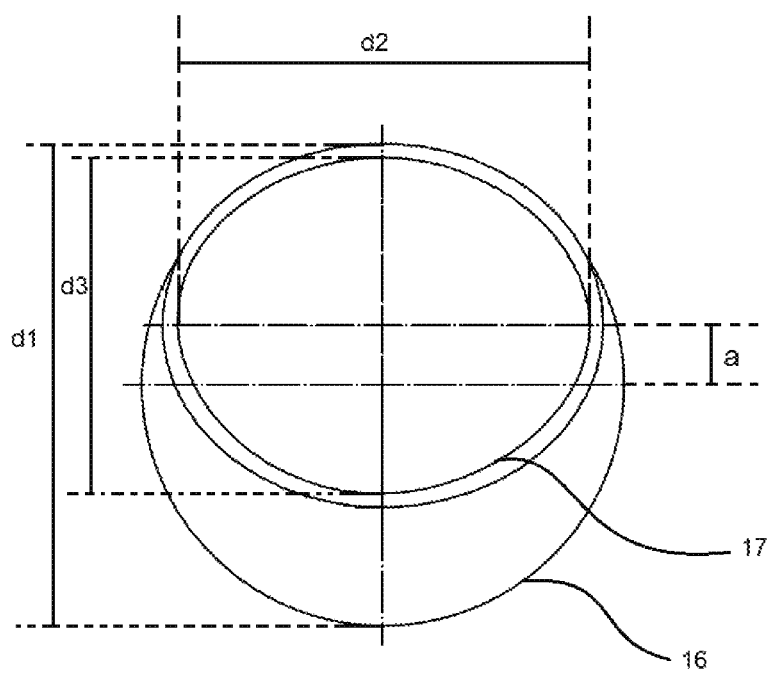

FIG. 4 Detail of FIG. 3 marked with A in FIG. 3, which only shows the view of the distal face of the shaft FIG. 5 Working channel of the endoscope according to FIG. 1 in a side view FIG. 6 View of the working channel as shown in FIG. 5 in the viewing direction marked with B in FIG. 5

DESCRIPTION OF THE MODEL EMBODIMENT

FIGS. 1 to 6 represent a model embodiment of an endoscope 1. The endoscope has an elongated shaft 2 and a main body 3. The shaft 2 extends along a longitudinal axis 4. The shaft has a proximal end 5 facing the main body 3 and a distal end 6 facing away from the main body 3. The shaft 2 is housed in the main body 3 with its proximal end 5. One image guide 7, two fibre-optic light guides 8, two flushing channels 9 and one working channel 10 run through the shaft 2. Image guide 7, fibre-optic light guides 8, flushing channels 9 and working channel 10 lead to the face of the distal end 6 of the shaft 2. This is especially discernible in FIG. 4. The working channel 10 extends from the distal end 6 of the shaft 2 to the face of the main body 3 facing away from the shaft 2. The distal end 11 of the working channel 10 is located on the distal end 6 of the shaft 2. The proximal end 12 of the working channel 10 is located on the face of the main body 3 facing away from the shaft 2. On the proximal end 12 an instrument not shown in the drawing can be inserted in the working channel 10 and pushed to the distal end 11 of the working channel 10. The fibre-optic light guides 8 lead to a light guide connection 13 on the main body 3 at which a light source not shown in the drawing can be connected via an additional fibre-optic light guide. Both flushing channels lead to two flushing channel connections 14 on the main body 3. The image guide 7 extends in the main body 3 to an eyepiece 15.

In FIG. 1 the working channel 10 is shown in a longitudinal section. The cross-section areas of the working channel 10 are shown in FIG. 6. On its proximal end 12 the working channel 10 has a circular cross-section area 16. On its distal end 11 the working channel 10 has an oval cross-section area 17. The oval cross-section extends from the distal end 11 to a transitional area 18 arranged in the main body 3. From the transitional area 18 to the proximal end 12 the working channel 10 has a constant circular cross-section. The transitional area 18 has a conical form.

FIG. 5 shows the working channel 10 in a view from the side. The working channel 10 is formed by a pipe that is drawn with the transitional area 18 during production. In its section with an oval cross-section the working channel 10 extends along a first working channel longitudinal axis 19. In its section with a circular cross-section the working channel extends along a second working channel longitudinal axis 20. The two working channel longitudinal axes 19, 20 are parallel to one another. They have a distance 'a'.

In FIG. 6 the circular cross-section area 16 and the oval cross-section area 17 are shown in comparison. Because the pipe that forms the working channel 10 has a certain wall thickness, the inner cross-section and the outer-cross section are shown in FIG. 6 for the oval cross-section. The working channel 10 is formed by the inner cross-section. The diameter of the circular cross-section area 16 is indicated with $d_1$. The oval cross-section area 17 has a greatest diameter $d_2$ and a smallest diameter $d_3$. $d_3$ is smaller than $d_2$. Furthermore, the greatest diameter $d_2$ is smaller than $d_1$. The first working channel longitudinal axis 19 extends through the point of intersection of the greatest diameter $d_2$ with the smallest diameter $d_3$ of all oval cross-section areas. The second working channel longitudinal axis 20 extends through the centre point of all circular cross-section areas. The distance 'a' between the two working channel longitudinal axes 19, 20 is slightly smaller than the difference between $d_1/2$ and $d_3/2$. The first and second longitudinal axes 19, 20 are parallel to one another. They also run parallel to the longitudinal axis 4 of the shaft that is shown in FIG. 1.

All features of the invention can be material to the invention both individually and in any combination.

REFERENCE NUMBERS

1 Endoscope
2 Shaft
3 Main body
4 Longitudinal axis
5 Proximal end of the shaft
6 Distal end of the shaft
7 Image guide
8 Fibre-optic light guide
9 Flushing channel
10 Working channel
11 Distal end of the working channel
12 Proximal end of the working channel
13 Light guide connection
14 Flushing channel connection
15 Eyepiece
16 Circular cross-section area
17 Oval cross-section area
18 Transitional area
19 First working channel longitudinal axis
20 Second working channel longitudinal axis

The invention claimed is:

1. An endoscope
with a shaft (2) that is designed as a flexible or rigid elongated hollow body,
with a distal end (6) and a proximal end (5) of the shaft (2),
with a main body (3) which houses the shaft (2) on its proximal end (5),
with an image guide (7) and a working channel (10) which extend through the shaft (2) from the distal to the proximal end, continuing into the main body (3),
wherein the working channel (10) receives an instrument,
with a distal end (11) of the working channel (10) which is located in the area of the distal end (6) of the shaft (2),
with a proximal end (12) of the working channel (10) which is located in or on the main body (3),
wherein the cross-section of the working channel (10) is circular at its proximal end (12) and non-circular at its distal end (11),
wherein the working channel (10) has a transitional area (18) in which the circular cross-section transitions into the non-circular cross-section, and
wherein the transitional area (18) is located in the main body (3).

2. The endoscope according to claim 1, wherein the cross-section area of the working channel (10) is larger at the proximal end (12) than at the distal end (11).

3. The endoscope according to claim 1, wherein the section of the working channel (10) that extends beyond the main body (3) into the shaft (2) has a continuous non-circular cross-section with a constant cross-section area.

4. The endoscope according to claim 1, wherein the working channel (10) has a continuous circular cross-section with a constant cross-section area between the transitional area (18) and the proximal end (12).

5. The endoscope according to claim 1, wherein the transitional area (18) is generally conical or tapered.

6. The endoscope according to claim 1, wherein the non-circular cross-section area (17) of the working channel (10) has a greatest diameter and a smallest diameter at its distal end (11), and wherein the greatest diameter is smaller than or equal to the diameter of the circular cross-section area (16) of the working channel (10) at its proximal end (12).

7. The endoscope according to claim 6, wherein the center point of the non-circular cross-section area (17) of the working channel (10) at its distal end (11) corresponds to the point of intersection from the greatest diameter and the smallest diameter.

8. The endoscope according to claim 7, wherein the working channel (10) has a first working channel longitudinal axis (19) in its section with non-circular cross-section that extends through the center points of the non-circular cross-section areas (17), and wherein the working channel (10) has a second working channel longitudinal axis (20) in its section with circular cross-section that extends through the center points of the circular cross-section areas (16).

9. The endoscope according to claim 8, wherein the extension of the first working channel longitudinal axis (19) coincides with the second working channel longitudinal axis (20).

10. The endoscope according to claim 8, wherein the extension of the first working channel longitudinal axis (19) is parallel to the second working channel longitudinal axis (20) and has a distance 'a' from the second working channel longitudinal axis (20), wherein a is not zero.

11. The endoscope according to claim 10, wherein the distance 'a' is less than or equal to the difference from half of the diameter of the circular cross-section area (16) of the working channel (10) at its proximal end (12) and half of the smallest diameter of the non-circular cross-section area (17) of the working channel (10) at its distal end (11).

12. The endoscope according to claim 1, wherein the non-circular cross-section at the distal end of the working channel is oval.

\* \* \* \* \*